(12) United States Patent
Devenish et al.

(10) Patent No.: US 9,358,256 B2
(45) Date of Patent: Jun. 7, 2016

(54) GAP-PATTERNED FOAM DRESSING AND METHOD OF MAKING SAME

(71) Applicant: LINKS MEDICAL PRODUCTS, INC., Irvine, CA (US)

(72) Inventors: Greg Devenish, Farnborough (GB); Howard Kenneth Payne, Horsham (GB)

(73) Assignee: Links Medical Products, Inc., Irvine, CA (US)

( * ) Notice: Subject to any disclaimer, the term of this patent is extended or adjusted under 35 U.S.C. 154(b) by 265 days.

(21) Appl. No.: 13/939,829

(22) Filed: Jul. 11, 2013

(65) Prior Publication Data
US 2015/0018791 A1 Jan. 15, 2015

(51) Int. Cl.
*A61F 13/15* (2006.01)
*A61M 27/00* (2006.01)
*A61K 35/644* (2015.01)
*A61F 13/00* (2006.01)

(52) U.S. Cl.
CPC ......... *A61K 35/644* (2013.01); *A61F 13/00021* (2013.01); *A61F 13/00042* (2013.01); *A61F 13/00063* (2013.01); *A61F 13/00991* (2013.01); *A61F 2013/00314* (2013.01); *A61F 2013/00331* (2013.01)

(58) Field of Classification Search
CPC ............ A61F 2013/00314; A61F 2013/00331; A61F 2013/00151; A61F 2013/00285
USPC .................. 604/360, 543, 308, 367, 379, 380
See application file for complete search history.

(56) References Cited

U.S. PATENT DOCUMENTS

| | | |
|---|---|---|
| 3,767,784 A | 10/1973 | Gluck |
| 5,064,653 A | 11/1991 | Sessions et al. |
| 5,456,745 A | 10/1995 | Roreger et al. |
| 5,536,263 A | 7/1996 | Rolf et al. |
| 5,807,295 A | 9/1998 | Hutcheon et al. |
| 6,190,689 B1 | 2/2001 | Hoffmann et al. |
| 6,355,858 B1 | 3/2002 | Gibbins |
| D475,856 S | 6/2003 | Karul et al. |
| 6,605,751 B1 | 8/2003 | Gibbins et al. |
| 6,897,349 B2 | 5/2005 | Gibbins et al. |
| 7,285,576 B2 | 10/2007 | Hyde et al. |
| 7,288,265 B1 | 10/2007 | Rolf |
| D601,812 S | 10/2009 | Bruun et al. |
| 7,691,829 B2 | 4/2010 | Petito et al. |
| 7,704,934 B2 | 4/2010 | Lepilleur |

(Continued)

OTHER PUBLICATIONS

Molan, P.C., "The Role of Honey in the Management of Wounds", Journal of Wound Care, September, vol. 8, No. 8, pp. 415-418 (1999).

(Continued)

*Primary Examiner* — Jacqueline Stephens
(74) *Attorney, Agent, or Firm* — Jerry R. Potts; James R. McDaniel

(57) ABSTRACT

A gap-patterned wound dressing, including a patterned foam structure having a gap patterned side and a non-gap patterned side, wherein the gap patterned side includes a pattern of foam gaps disposed between foam areas dosed with honey, where the pattern of foam gaps is formed by the honey dosed areas; and wherein a wound in contact with the gap patterned side discharges an exudate which substantially collects in the individual ones of the foam gaps causing honey in the individual ones of the honey dosed areas to be substantially dispersed throughout a wound treatment zone.

24 Claims, 7 Drawing Sheets

(56) References Cited

U.S. PATENT DOCUMENTS

| | | |
|---|---|---|
| 7,714,183 B2 | 5/2010 | Caskey |
| 7,731,954 B2 | 6/2010 | Davis |
| 7,750,201 B2 | 7/2010 | Patel et al. |
| 7,820,872 B2 | 10/2010 | Gregory et al. |
| 7,919,589 B2 | 4/2011 | Ward et al. |
| 8,021,650 B2 | 9/2011 | Tamareselvy et al. |
| D648,439 S | 11/2011 | Greener et al. |
| 8,080,703 B2 | 12/2011 | Marcussen |
| 8,128,947 B2 | 3/2012 | Jones et al. |
| 8,227,656 B2 | 7/2012 | Svetlik |
| 2004/0010215 A1 | 1/2004 | Gibbins |
| 2004/0121020 A1 | 6/2004 | Moloney |
| 2004/0127826 A1* | 7/2004 | Caskey ............ 602/41 |
| 2004/0127837 A1* | 7/2004 | Sigurjonsson .......... 602/42 |
| 2006/0064049 A1* | 3/2006 | Marcussen ............ 602/42 |
| 2008/0107734 A1 | 5/2008 | Marraccini |
| 2008/0228123 A1 | 9/2008 | Moore et al. |
| 2011/0135726 A1 | 6/2011 | Munro et al. |
| 2011/0189287 A1 | 8/2011 | Abbott et al. |
| 2012/0078153 A1 | 3/2012 | Russell et al. |
| 2012/0136328 A1 | 5/2012 | Johannison et al. |

OTHER PUBLICATIONS

Mathew, et al. "Wound Management Using Honey," Compendium, vol. 24, No. 1, Jan. 2002, pp. 53-60.

Internet Website: "What is Foam Dressing?", (2012) Wise Greek. Accessed Aug. 22, 2012 at http://www.wisegeek.com/what-is-a-comfeel-dressing.htm.

Internet Website: "A Material Based on Sharkskin Stops Bacterial Breakouts," (2009) Popsci. Accessed, Aug. 22, 2012 at http://www.popsci.com/science/article/2009-10/saving-skin.

\* cited by examiner

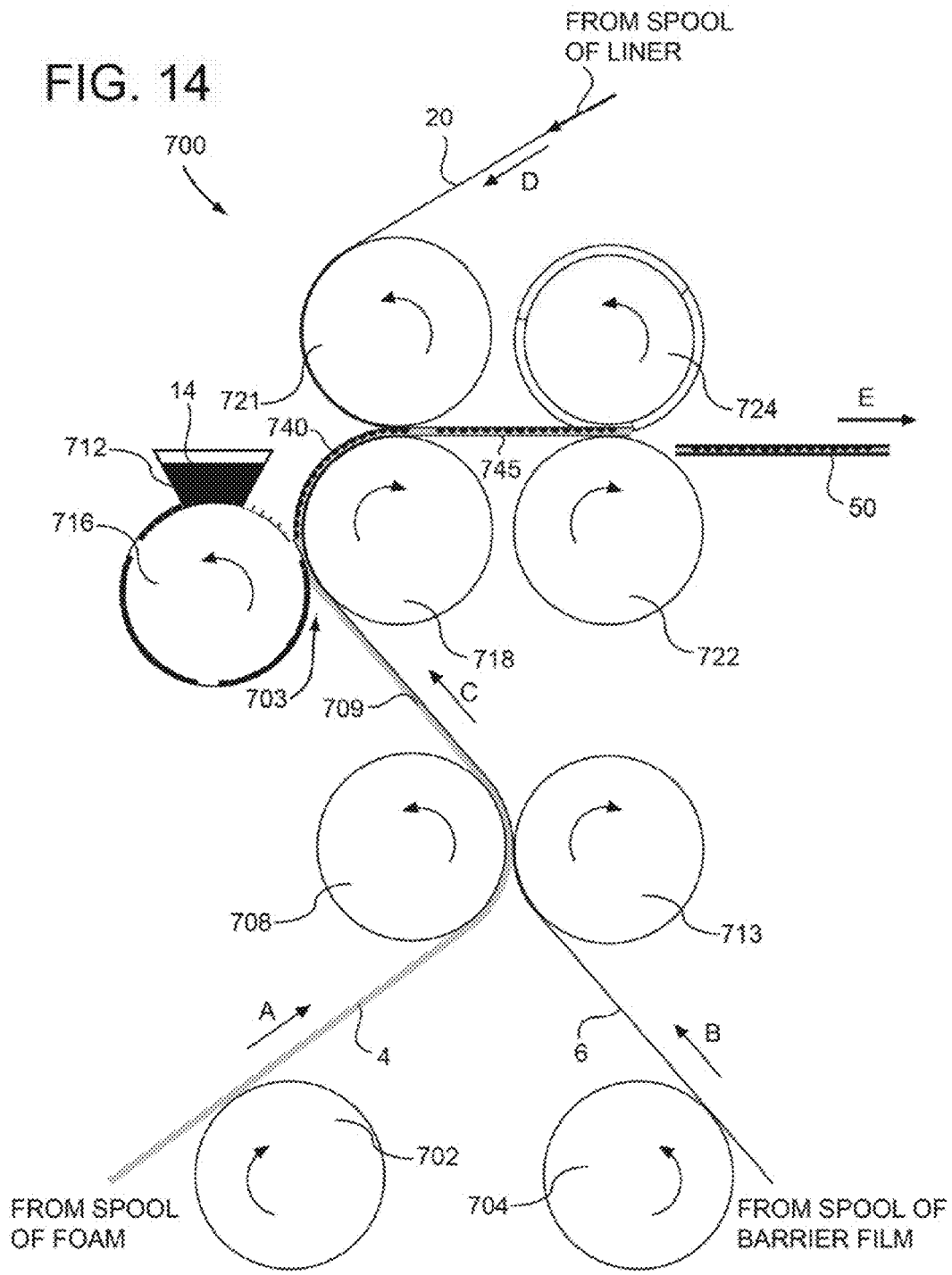

GAP-PATTERNED FOAM DRESSING AND METHOD OF MAKING SAME

FIELD OF THE INVENTION

This invention relates generally to medical grade foam dressings and more particularly to a gap-patterned medical grade foam dressing.

BACKGROUND OF THE INVENTION

Prior to the present invention, as set forth in general terms above and more specifically below, it is known, that due to the rise of antibiotic-resistant bacteria, honey is starting to be used to combat these bacteria. Furthermore, it is known to use Manuka honey in wound dressings because of its antibacterial and antimicrobial properties. See for example, U.S. Pat. RE 42,755 to Molan, U.S. Pat. No. 7,714,183 to Caskey, U.S. Pat. No. 7,288,265 to Rolf, and U.S. Pat. No. 6,956,144 to Molan. While the use of Manuka honey may have been generally satisfactory, there is nevertheless a need for a new and improved gap-patterned wound dressing, including a patterned foam structure having a gap patterned side and a non-gap patterned side, wherein the gap patterned side includes a pattern of foam gaps disposed between foam areas dosed with honey, where the pattern of foam gaps is formed by the honey dosed areas; and wherein a wound in contact with the gap patterned side discharges an exudate which substantially collects in the individual ones of the foam gaps causing honey in the individual ones of the honey dosed areas to be substantially dispersed throughout a wound treatment zone It is a purpose of this invention to fulfill this and other needs in the art in a manner more apparent to the skilled artisan once given the following disclosure.

SUMMARY OF THE INVENTION

A feature of the present invention is gap-patterned wound dressing, including a patterned foam structure having a gap patterned side and a non-gap patterned side, wherein the gap patterned side includes a pattern of foam gaps disposed between foam areas dosed with honey, where the pattern of foam gaps is formed by the honey dosed areas; and wherein a wound in contact with the gap patterned side discharges an exudate which substantially collects in the individual ones of the foam gaps causing honey in the individual ones of the honey dosed areas to be substantially dispersed throughout a wound treatment zone.

Another feature of the present invention is the provision of a gap-patterned foam structure which includes a dry edge portion disposed substantially along an outer side edge of the structure which allows for ease of handling during application without contacting honey or exudates disposed in the wound dressing.

Another feature of the present invention is the provision of the individual ones of the honey dosed areas being hexagon-shaped areas.

Another feature of the present invention is the provision of the use of a medical grade, absorbent, and porous polymeric foam.

Another feature of the present invention is the provision of the use of a medical grade polyether polyurethane foam.

Another feature of the present invention is the provision wherein the foam includes a thickness that is sufficient to hold a specific amount of honey about 50% by total weight to about 75% by total weight of the foam structure and honey, in combination.

Another feature of the present invention is the provision wherein the thickness of the foam structure is substantially between 0.1 mm and 25 mm.

Another feature of the present invention is the provision wherein the honey dosed areas are dosed with honey selected from a group of different honeys consisting of: medical grade Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, and Kamahi honeys.

Another feature of the present invention is the provision wherein a width of the foam gap patterns is substantially between 0.05 mm and 100 mm.

Another feature of the present invention is the provision wherein a top portion of each foam gap is layered with a minimal trace of honey.

Another feature of the present invention is the provision wherein the non-gap patterned side of the patterned foam structure includes a barrier.

Another feature of the present invention is the provision wherein the barrier is secured to the non-gap patterned side of the patterned foam structure by an adhesive.

Another feature of the present invention is the provision wherein the wound dressing further includes a protective liner located substantially along the gap patterned side of the foam structure.

Another feature of the present invention is the provision wherein the protective liner is secured to the gap patterned side of the patterned foam structure by the thin layer of honey.

Another feature of the present invention is the provision wherein the dressing is substantially enclosed in a protective pouch such that the pouch provides adequate moisture barrier properties to protect the dressing.

A feature of the present invention is a method for preparing a gap-patterned foam dressing, including the step of applying specific amounts of honey to a substantially flat flexible, planar sheet of foam such that a pattern of non-honey dosed areas are formed along the patterned side of the foam structure.

Another feature of the present invention is the provision wherein the applying step is further comprised of: applying the honey by coating, dosing, pasting, impregnating, injecting, pouring, spraying, transferring, printing (all methods) including lithography, stenciling, flexography, gravure, infusion, and rotogravure.

Another feature of the present invention is the provision wherein the method includes the step of attaching a barrier to a non-gap patterned side of the foam structure.

Another feature of the present invention is the provision wherein the method further includes the step of locating a protective liner substantially adjacent to the gap patterned side of the foam structure.

Another feature of the present invention is the provision wherein the method further includes the step of placing the dressing substantially within a pouch so as to provide a moisture barrier for the dressing.

A feature of the present invention is a gap patterned wound dressing, including a patterned foam structure having a gap patterned side and a non-gap patterned side, wherein the gap patterned side includes a pattern of foam gaps disposed between foam areas dosed with honey, where the pattern of foam gaps is formed by the dosed honey areas; wherein a wound in contact with the gap patterned side discharges an exudate which substantially collects in the individual ones of the foam gaps causing honey in the individual ones of the honey dosed areas to be substantially dispersed throughout a wound treatment zone; and wherein the foam includes a thickness that is sufficient to hold a specific amount of honey about 50% by total weight to about 75% by total weight of the foam structure and honey, in combination.

A feature of the present invention is a honey dosed foam wound dressing including a composite fiber reinforced foam structure having a honey dosed side and a non-honey dosed side, wherein the honey dosed side is dosed with a coat of honey of a sufficient thickness to hold a specific amount of honey less than about 50% by weight of the total weight of wound dressing.

Another feature of the present invention is a honey dosed wound dressing, wherein the composite fiber reinforced foam has an uncompressed density of approximately between 95-150 kg/m$^3$.

A feature of the present invention is a honey dosed gauze wound dressing having a honey dosed gauze structure having a plurality of gaps located on the honey dosed side, such that honey is substantially located within the gauze structure around the plurality of gaps.

Another feature of the present invention is a honey dosed gauze wound dressing, wherein the gaps create a void such that substantially no honey is located within the gaps.

A feature of the present invention is a honey dosed gauze wound dressing, wherein the gauze structure includes a pouch in which an absorbent pad is located and a honey dosed side and a substantially non-honey dosed side, wherein a wound in contact with the honey dosed side discharges an exudate which substantially collects in the absorbent pad, and wherein the non-honey dosed side is provided with a breathable barrier.

Another feature of the present invention is a honey dosed gauze wound dressing, wherein the dressing further includes an anti-tackiness layer located substantially on at least one side of the wound dressing.

Another feature of the present invention is the provision wherein the dressing further includes a protective liner located substantially along at least one side of the wound dressing.

Another feature of the present invention is a honey dosed gauze wound dressing, wherein the anti-tackiness layer further includes silicon oil, fluorocarbon coated liners and embossed or un-embossed polymer liners.

The preferred honey dosed, patterned foam dressing, according to various embodiments of the present invention, offers the following advantages: ease of use; improved dressing strength; reduced dressing weight; increased efficiency and controlled lay down of honey; increased ability to deliver an equal measure of honey across the wound bed; increased ability to promote controlled, naturally occurring osmotic delivery action of the honey onto the wound bed; increased rate of absorption of exudates while allowing honey stored within the honey-dosed area to flow naturally onto the wound; and improved ease of handling of the dressing. In fact, in many of the preferred embodiments, these factors of improved strength, reduced weight, increased lay down efficiency, increased honey loading, increased honey delivery, increased osmotic delivery action, increased exudate absorption ability, and improved ease of handling are optimized to an extent that is considerably higher than heretofore achieved in prior, known honey-based wound dressings.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 14 is a schematic illustration of the construction of a gap-patterned medical grade foam dressing, constructed according to the present invention.

DETAILED DESCRIPTION OF PREFERRED EMBODIMENTS

Figure 1:
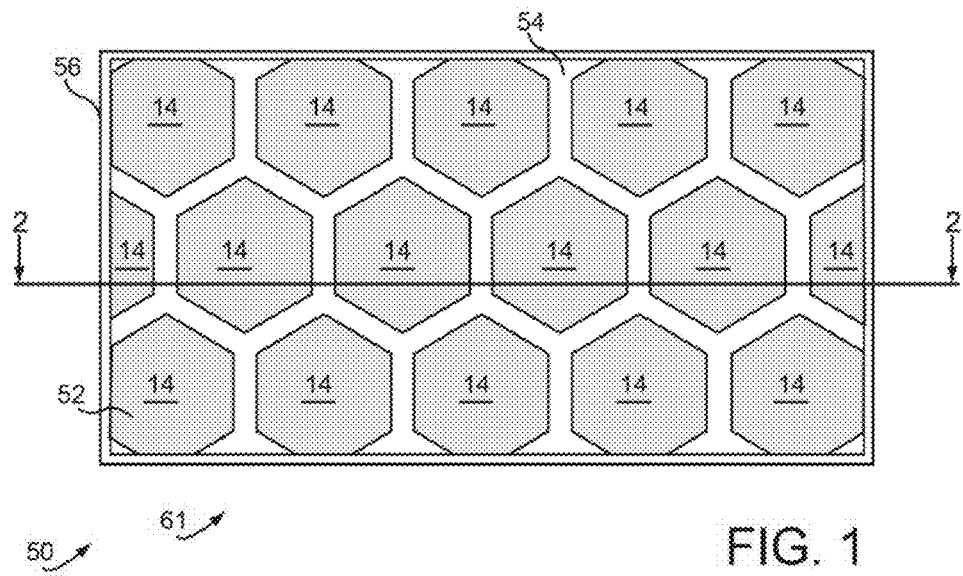
FIG. 1 is a top view of a gap-patterned medical grade foam dressing, constructed according to the present invention.
Figure 2:
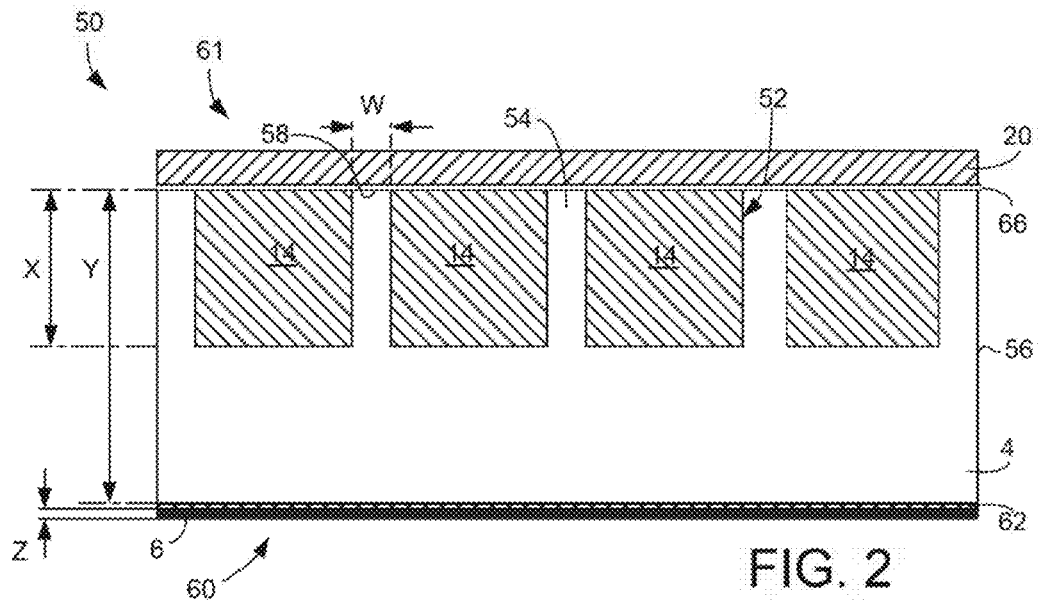
FIG. 2 is a cross-sectional view of the gap-patterned medical grade foam dressing taken substantially along line 2-2 of FIG. 1.
Figure 3:
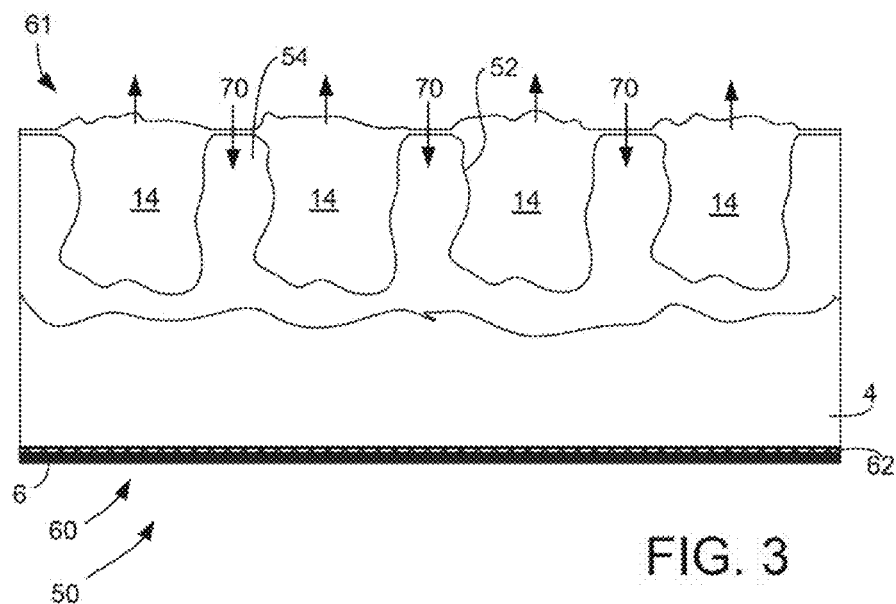
FIG. 3 is a diagrammatic illustration of the gap-patterned medical grade foam dressing of FIG. 2, wherein an exudate has caused the foam gap patterned areas to swell and expand thereby dispersing the honey out of the honey deposits in the foam.

Referring now to the drawings and more particularly to FIGS. 1-3, there is illustrated a gap-patterned medical grade foam dressing 50, which is constructed in accordance with the present invention. As will be explained hereinafter in greater detail, the dressing 50 is constructed to provide a pumping action that pulls or draws exudates from a wound into the dressing 50 and disperses a precise dose of honey 14 from the dressing 50 throughout the wound treatment zone. The advantages of foam dressing 50 are the improved management of exudates through the foam gap patterned areas in dressing 50, the swelling of the foam gap patterned areas supports natural osmotic pump action of the honey, tackiness in dressing 50 is reduced because there are gaps between the honey-dosed areas, the honey is dispersed faster and more evenly into the wound, dry edges around dressing 50 allow for easy handling of the dressing 50 and protect the dressing from accidental damage, and the single-sided application of honey to dressing 50 presents the honey dose to the wound face of dressing 50 rather than wasting unused honey on the bandage side of dressing 50.

Considering now the gap-patterned medical grade foam dressing 50, in greater detail with reference to FIGS. 1-3, the gap-patterned medical grade foam dressing 50 generally includes a flexible sheet of polyether polyurethane foam 4 having a non-wound contact side indicated generally at 60 (FIG. 2) and a wound contact side indicated generally at 61 (FIG. 2). The non-wound side 60 of the dressing 50 is protected with a breathable barrier 6, having a (Z) thickness of about 30 microns, as best seen in FIG. 2. The barrier 6 is composed of a sheet of breathable polyurethane. While barrier 6 is cosmetic, its purpose is to protect the dressing 50 from debris and liquid contamination.

Dressing 50 may also be provided with a dry picture frame edge 56 (FIGS. 1 and 2) which facilitates ease of handling of the dressing 50 during the wound dressing application process. Foam 4 is medical grade foam that is highly absorbent, flexible, porous and fully breathable to help facilitate the formation of a moist wound environment which is highly conducive for body healing purposes.

As best seen in FIG. 2, the wound contact side 61 of the dressing 50 is provided with a patterned plurality of foam gaps 54 interspersed with a patterned plurality of honey dosed foam areas 52. The foam gaps 54 are formed in the foam 4 when the foam 4 is dosed with honey 14, which is an important feature of the present invention. That is, the patterns of honey dosed foam areas 52 and the patterns of non-dosed foam gaps 54 cooperate with one another to create a pumping, push-pull action that allows the dressing 50 to: 1) absorb or pull wound exudates from a treated wound area into the non-dosed foam gaps 54; and 2) to disperse substantially the totality of the honey 14 in the honey dosed foam areas 52 onto the treated wound area covered by the dressing 50.

While in the preferred embodiment of the present invention, the patterned dressing 50 is illustrated as being provided with a gapped honeycomb pattern, it should be appreciated by those skilled in the art, that any suitable gap-patterned shape can be employed, although the gapped hexagon pattern is the preferred shape. Studies on the geometry of the honeycomb pattern explain that no other shape can create more space. Circles for instance leave spaces, and squares make smaller areas. In addition, the hexagon structure reduces the weight of dressing 50.

Furthermore, the honeycomb design allows for the most efficient and controlled lay down of honey 14 onto the dressing 50, creating roughly 300 honey-dosed areas 52 in a 10×10 cm dressing. It is calculated that each honey dosed area 52 will contain around 0.025 g of honey 14. The gap-patterned foam matrix also allows for the dressing 50 to remain flexible and pliable making it easily conformable to the wound.

With respect to foam 4, foam 4 preferably is constructed of any suitable medical grade, breathable, absorbent, flexible and porous polymeric foam, preferably, medical grade polyether polyurethane foam. It is to be understood that the foam should create a moist wound environment which triggers the body's natural healing ability. Finally, foam 4 should be sufficiently absorbent to hold deposits of honey 14 in place but not so absorbent as to allow the deposits of honey 14 to run into the non-dosed foam walls or foam gaps 54 disposed between the honey deposits.

As shown more clearly in FIG. 2, foam 4 should have a thickness in a range (Y) of between 0.1 mm minimum to about a maximum of 25 mm, with a preferable thickness of approximately 4 mm.

Also as shown more clearly in FIG. 2, the non-dosed foam walls or gaps 54 of patterned foam dressing 50 should have a thickness in a range (W) of between 0.05 mm minimum to about a maximum of 100 mm, with a preferable thickness of 1 mm. It is to be understood that the thickness (W) should be of a range which allows sufficient absorption and swelling, while also maintaining the cosmetic look and separation of honey-dosed areas 52 within the gap-patterned foam dressing 50.

With respect to the honey 14 utilized to dose the foam 4, medical grade Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, and Kamahi honeys are all known to contain superior anti-bacterial and antiinflammatory factors and thus are preferred honeys for the dressing 50. Manuka honey also has the ability to have a rapid deodorizing effect with patients having malodorous fungating wounds, which could be due to the inhibition of anaerobic bacterial growth. Finally, the high sugar levels in honey may well result in osmotic pressure that promotes autolytic debridement and, for these reasons, Manuka honey is the preferred honey for use in the dressing 50. The high sugar levels in the honey result in osmotic pressure that promotes autolytic debridement. The terminology "osmotic pressure" is defined herein to mean the pressure required to maintain equilibrium of two solutions, with no net movement between one solution (e.g., a solvent) and the other solution. The terminology "autolytic debridement" is defined herein to mean a process by which the body's own enzymes and moisture is used to re-hydrate, soften and liquefy hard eschar and slough (i.e., dry scab and dead tissue).

As shown in FIG. 2, the gap-patterned foam dressing 50 has a dosed honey depth in a range (X) which is between approximately a minimum of 0.1 mm to about a maximum of 24.9 mm, with a preferred dose depth of about 3 mm.

Regarding the dosage of honey 14 in dressing 50, the ratio of honey weight to total weight of dressing 50 will vary depending upon the size and style of dressing 50. Preferably, the depth of the patterned foam dressing 50 is sufficient to hold a specific amount of honey 14 of between 50%-75% of honey 14 to the total weight of dressing 50. Also, it is to be understood that the target dose of honey 14 for a 4 inch by 4 inch (10 cm×10 cm) dressing 50 is between 0.5 g to 100 g, with the preferable dosage being 8-10 g. However, it is to be understood that balance is critical in that overdosing dressing 50 with honey 14 may result in a functional failure of dressing 50 because the foam structure 4 may become over saturated thereby decreasing the rate at which dressing 50 absorbs exudates. It is to be understood that it is not necessary to have a three-dimensional shape with a flat bottom. The bottom could taper off into a point.

The majority of the honey 14 is contained within the dosed areas 52 but the surface of the dressing 50 has a micro thin or minimal trace layer 58 of honey 14, which is of such a minimal amount that the top surface is not sticky and is easy to handle. Moreover, the dressing 50 has been designed with dry edges 56 (FIGS. 1 and 2) around all four sides of dressing 50, thereby reducing tackiness of dressing 50. This allows for easy handling relative to placing dressing 50 on a wound once the protective liner 20 (FIG. 2) has been removed and the dressing face is exposed. It is to be understood that tackiness of dressing 50 is reduced because there are gaps between the honey-dosed areas. The dosing is controlled, thus not saturating the dressing 50. The honey 14 is dosed into the areas 52 thus creating optimal storage of the honey 14 within the honey-dosed areas 52. It is to be further understood that dry edges 56 can allow extra capacity for quick ingress of exudates on higher exuding wounds. Finally, it is to be understood that dressing 50 may not include dry edges 56.

It is to be understood that honey 14 is prevented from oozing off of dry edges 56 because the moisture within honey 14 is reduced once it is dosed into the foam 4.

As shown more clearly in FIGS. 2-3, foam walls or gaps 54 are designed to absorb exudates from the wound down through and into the areas between honey dosed areas 52 at the rear of the dressing 50. In this manner, areas 52 disperse the honey 14 throughout the wound treatment zone through the naturally occurring osmotic action. This design allows for an even delivery of honey 14 across the wound bed.

With respect to FIG. 2, barrier 6, preferably is any suitable, breathable barrier constructed of polyurethane film. While barrier 6 is cosmetic, the purposes of barrier 6 are to provide a barrier to stop bacterial infection from outside of the wound, to stop any honey 14 from potentially bleeding through barrier 6, to protect the dressing 50 from debris or liquid contamination and to stop exudates from bleeding through dressing 50. Preferably, the thickness (Z) of barrier 6 is around 30 microns. Barrier 6 is, preferably, conventionally pre-coated with a medical grade medium tack acrylic or silicone pressure sensitive adhesive 62. It is to be understood that barrier 6 can also be attached to gap-patterned dressing 50 by conventional heat bonding.

Located over honey 14 in patterned dressing 50 is a conventional, peelable liner 20 which is attached to patterned dressing 50 by thin micro or minimal trace layer 58 of honey 14.

As shown more clearly in FIG. 3, an important feature of the patterned dressing 50 is the foam walls or gaps 54 between the honey-dosed areas 52. The foam walls or gaps 54 in the patterned dressing 50 permit exudates 70 (water) to pass through and between the honey-dosed areas 52 and collect in foam walls or gaps 54. This enhances a naturally occurring osmotic pumping action by causing the foam walls or gaps 54 to swell, thereby taking up space and applying pressure to the honey-dosed areas 52. As can be seen in FIG. 3, exudates 70 cause foam walls or gaps 54 to expand out which, in turn, applies pressure to the adjacent honey-dosed areas 52. As a result, the honey 14 is dispersed out of honey-dosed areas 52. This provides a steady supply of honey 14 throughout the wound treatment zone. This action will continue until the honey 14 is depleted which results in substantially the complete dispersion of the honey 14 from the dressing 50 throughout the wound treatment zone.

Figure 4:
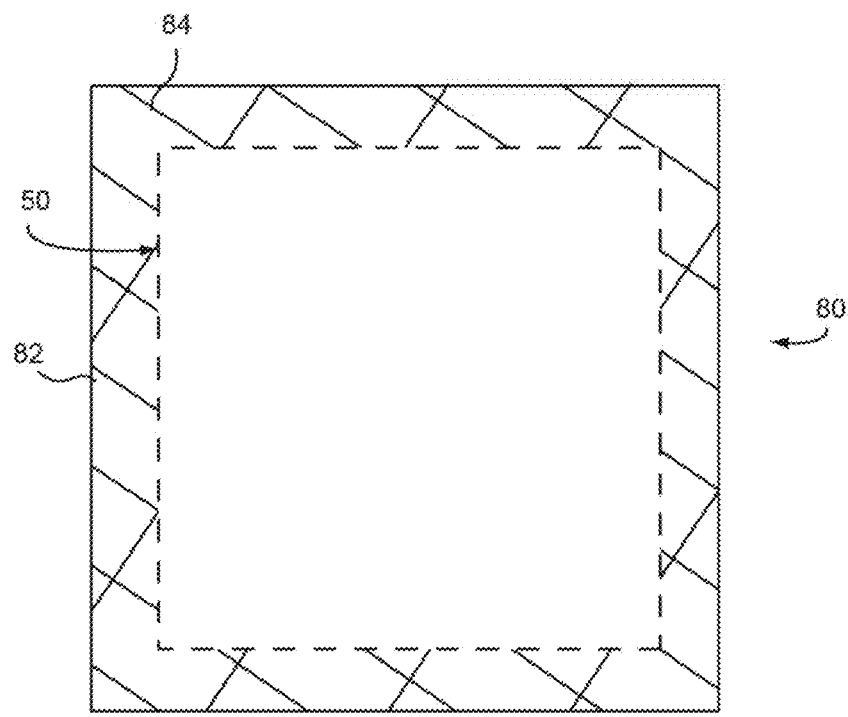
FIG. 4 is a schematic illustration of a pouch which contains a sterile, gap-patterned medical grade foam dressing, constructed according to the present invention.

With respect to FIG. 4, there is illustrated a complete dressing package 80 that includes a pouch 82 which encloses a gap-patterned, medical grade foam dressing 50. Pouch 82, preferably, is constructed of any suitable polyester and/or polyethylene material so as to provide a moisture barrier for dressing 50. Located around the perimeter of pouch 82 is a conventional, peelable adhesive 84 which allows the pouch 82 to be easily opened to remove dressing 50 but at the same time provides adequate moisture barrier properties to protect dressing 50.

The following EXAMPLE is being provided in order to more clearly disclose the inventive concepts of the present invention.

EXAMPLE

Foam is cut in order to form a 4 inch by 5 inch (10 cm by 12.5 cm) base for the dressing. Approximately, 8-11 grams of honey are dosed into a pattern of honey dosed areas and foam walls or gaps on the dressing base to form the dressing. The total weight of dressing (honey and foam structure) was determined to be 17 grams. After the dressing has been prepared, it is packed into a pouch 80 (FIG. 4) and conventionally passed through a gamma irradiation plant, which is validated to FDA & ISO standards. The gamma rays irradiate and kill any live pathogens that are present in any type of particulate or other form.

EXPERIMENT

In order to prove the efficacy of the present invention, the following experimental results are provided.

The purpose of the experiment is to establish the absorption rate of medical foam dressings dosed with honey. To compare the relative absorption rates between continuous surface dosed dressings with selective gap-pattern dosed dressings where areas of the foam surface are free from honey.

Apparatus
1. Samples of foam cut to 4×4 cm
2. Straight sided metal ring with 35 mm internal diameter
3. Water
4. Measuring Cylinder
5. Timer
6. Clean Flat Plate Method
1. Place dressing sample on to flat clean plate.
2. Place one open end of metal ring onto the dressing sample.
3. Measure 10 ml of water using a pipette or other suitable device.
4. Dispense contents of measuring device into the metal ring on the dressing.
5. Time how long it takes for the water to be fully absorbed into the dressing.
6. If the timing is difficult to adequately establish the absorption rate, use more or less water.
7. Thoroughly clean and dry the apparatus between each test.
8. Use the same amount of water for each test.

Results

Table I below shows the results obtained with a cross section of different samples:

TABLE I

| Dressing Type | Time in Seconds | | | | | | |
|---|---|---|---|---|---|---|---|
| | Test 1 | Test 2 | Test 3 | Test 4 | Test 5 | Test 6 | Average |
| Plain Control | 6.83 | 6.20 | 6.89 | 7.72 | | | 6.91 |
| 1.5 mm wall thickness | 9.98 | 8.29 | 9.24 | | | | 9.17 |
| 1.25 mm wall thickness | 8.56 | 11.21 | 8.57 | 8.96 | 7.66 | 8.34 | 8.88 |
| 1 mm wall | 11.12 | 11.86 | 10.30 | | | | 11.09 |

TABLE I-continued

|  | Time in Seconds | | | | | | |
| --- | --- | --- | --- | --- | --- | --- | --- |
| Dressing Type | Test 1 | Test 2 | Test 3 | Test 4 | Test 5 | Test 6 | Average |
| thickness 0.75 mm wall thickness | 14.79 | 11.49 | 13.09 | 15.29 | | | 13.67 |
| 0.5 mm wall thickness | 11.04 | 12.39 | 10.65 | 12.90 | | | 11.75 |
| Fully coated | 20.95 | 28.51 | 64.28 | 36.78 | 40.51 | 37.57 | 38.10 |

CONCLUSIONS

1. It appears from the above results that there is an increase in absorption rate where there are gaps between the honey deposits. This could be because the gaps provide a free channel for fluids to access the storage capacity of the foam.
2. Probably the presence of honey taking up capacity in the dressing, which would otherwise be available for absorption of fluids, has a proportional impact on the rate of absorption. This was suggested by the fact that the heavier dosed samples more quickly became saturated, with the excess fluid bleeding through the dressing and onto the plate around. This fluid had honey dispersed in it.
3. The 0.75 mm and 0.5 mm wall thickness samples were not completely clear of honey between the deposits, so the results appear to be skewed slightly.

Referring back to the drawings and more particularly to FIG. 14, a dressing construction apparatus 700 is illustrated, which apparatus 700 is constructed in accordance with the present invention. The apparatus 700 forms ribbons of foam dressing which are cut to a predetermined length and then packaged by means not shown for shipping purposes. In this regard, the results provide individual packages, such as a package 80 for containing the foam dressing 50.

Considering now the method of constructing the foam dressing 50 in greater detail, the apparatus 700 generally includes a first set of feed rollers indicated at 702 and 704, respectively. Feed roller 702 pulls into a construction path (A) a ribbon of foam 4 from a spool of foam (not shown). The ribbon of foam 4 has a width dimension required for the dressing 50. Feed roller 704 pulls into another construction path (B), a ribbon of barrier 6, whose width dimension corresponds to the width dimension of the ribbon of foam 4. The A construction path and the B construction path merge at the nip of a pair of laminating rollers 708 and 713, respectively. In this regard, the foam 4 and barrier 6 traverse along the direction of the construction paths A and B, respectively wherein the foam 4 and the barrier 6 are laminated together between the conventional laminating rollers 708 and 713 to create lamination 709. The laminating rollers 708 and 713 then cooperate with a pair of upstream rollers, namely a heated form roller 716 and a drive roller 718.

The heated form roller 716 is in fluid contact with a reservoir 712 of liquid honey 14 so when the surface of roller 716 passes by the reservoir 712, the conventionally heated roller 716 withdraws a predetermined amount of honey 14 from reservoir 712. It is to be understood that reservoir 712 can be located at other positions in apparatus 700. The honey coated roller 716 and drive roller 718 then engage the lamination 709 at their nip 703 which doses the foam side of lamination 709 such that a pattern of honey-dosed foam areas and a pattern of gap foam areas or walls are created in foam 4. A thin micro or minimal trace layer (58 in FIG. 2) of honey is deposited on the surface of the patterned surface of the patterned dosed foam 740 as it emerges from between rollers 716 and 718, respectively.

As the gap-patterned foam 740 emerges from between the heated form roller 716 and drive roller 718, it is further pulled upstream by a feed roller 721 which helps drive a liner 20 into a nip between the drive roller 718 and the feed roller 721 so that liner 20 is applied to the wet surface of the gap-patterned foam 740 to form a liner covered gap-patterned foam ribbon, indicated generally at 745. In this manner, liner 20 is retained on gap-patterned foam 740 by honey micro or minimal trace layer 58 (FIG. 2).

Next, ribbon 745 is pulled upstream by a drive roller 722 and a conventional rotary tool roller 724 which cooperate for die cutting the liner covered gap-patterned foam ribbon 745 as ribbon 745 passes between rollers 722 and roller 724, where it emerges as the dressing 50. It is to be understood that all rollers, as mentioned herein, turn at substantially the same surface speed as lamination 709, which can be anywhere between 1 m/minute and 15 m/minute. As mentioned previously, the dressing 50 then passes into a packaging mechanism (not shown) which packages individual ones of the dressing 50 in a pouch 80 package for ease of handling and radiation.

Although the preferred method of dosing foam with honey 14 to create or form a gap-patterned foam dressing 50 is illustrated by the apparatus 700 (FIG. 14), it is contemplated that honey 14 may be placed within honey-dosed areas 52 of dressing 50 by other types of apparatus for depositing honey, including but not limited to coating, dosing, pasting, impregnating, injecting, pouring, spraying, transferring, printing (all methods) including lithography, stencilling, flexography, gravure, infusion, and rotogravure. It is to be understood that a honey coating (not shown) maybe conventionally imprinted upon foam dressing 50 so that it appears to be a gap-patterned structure dosed with honey 14

Figure 5:
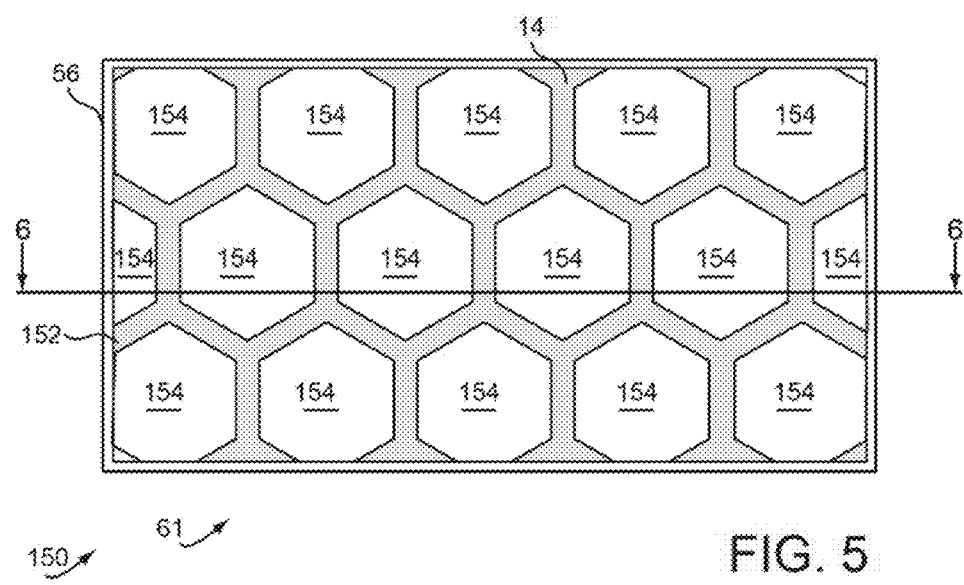
FIG. 5 is a top view of another gap-patterned foam dressing, constructed according to the present invention.
Figure 6:
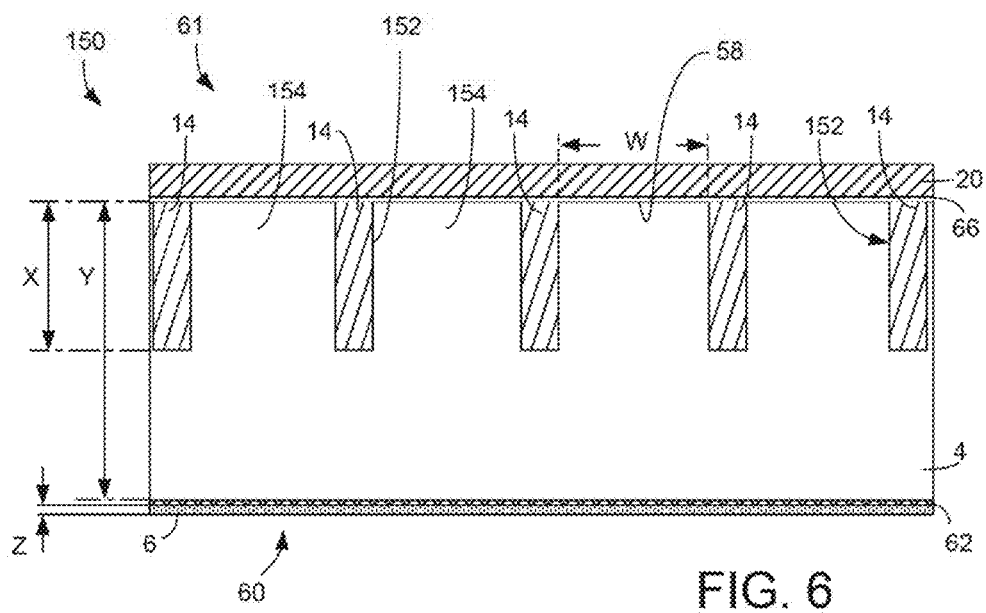
FIG. 6 is a cross-sectional view of the gap-patterned medical grade foam dressing of FIG. 5, taken substantially along line 6-6 of FIG. 5.
Figure 7:
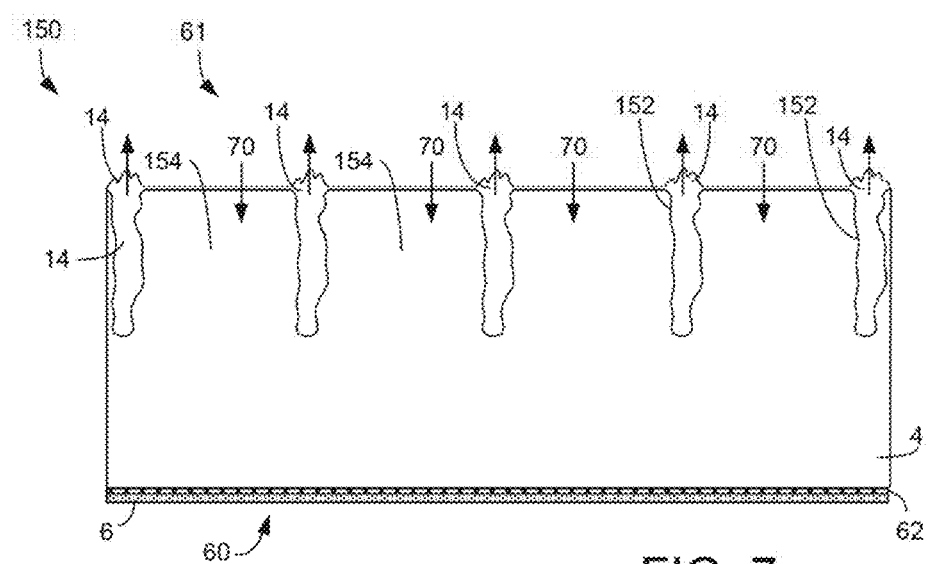
FIG. 7 is a diagrammatic illustration of the gap-patterned medical grade foam dressing of FIG. 6, wherein an exudate has caused the foam gap patterned areas to swell and expand thereby dispersing the honey out of the honey deposits in the foam.

Referring now to the drawings and more particularly to FIGS. 5-7 there is shown another gap-patterned medical grade foam dressing 150, which is constructed, in accordance with the present invention. The gap-patterned foam dressing 150 is the reverse of foam dressing 50. That is, the dressing 150 is provided with non-honey dosed gaps 154 having a hexagon shape such that non-honey dosed hexagon shaped gaps 154 are interspersed with honey dosed areas 152. Other than the patterned shapes as mentioned herein, the foam dressing 150 is substantially similar to foam dressing 50. Since foam dressings 50 and 150 are similar, it will suffice to mention that the foam dressing 150 is provided with a smaller dose of honey 14 since the honey 14 is dosed into smaller areas 152 than those of dosed area 52 in the dressing 50. Honey by weight in this embodiment therefore is 25-50% by weight as opposed to between 50-75% by weight. Also like dressing 50, dressing 150 is provided with a micro thin or minimal trace layer 58 of honey 14 on its upper surface which is also covered with a protective cover 20, just as was the case with dressing 50. The bottom surface of the foam 4 is further covered with a breathable barrier 6 which is adhered to the foam 4 by an adhesive 62, just as was the case with dressing 50.

As shown more clearly in FIG. 7, an important feature of the patterned dressing 150 is the foam walls or gaps 154 between the honey-dosed areas 152. The foam walls or gaps 154 in the patterned dressing 150 permit exudates 70 (water)

to pass through and between the honey-dosed areas 152 and collect in foam walls or gaps 154. This enhances a naturally occurring osmotic pumping action by causing the foam walls or gaps 154 to swell, thereby taking up space and applying pressure to the honey-dosed areas 152. As can be seen in FIG. 7, exudates 70 cause foam walls or gaps 154 to expand out which, in turn, applies pressure to the adjacent honey-dosed areas 152. As a result, the honey 14 is dispersed out of honey-dosed areas 152. This provides a steady supply of honey 14 onto the wound treatment zone. This action will continue until the honey 14 is dispersed inside and outside the dressing 150. As discussed earlier, the foam walls or gaps 154 of patterned foam dressing 150 should have a thickness in a range of between 0.05 mm minimum to about a maximum of 100 mm, with a preferable thickness of 4 mm.

Figure 8:
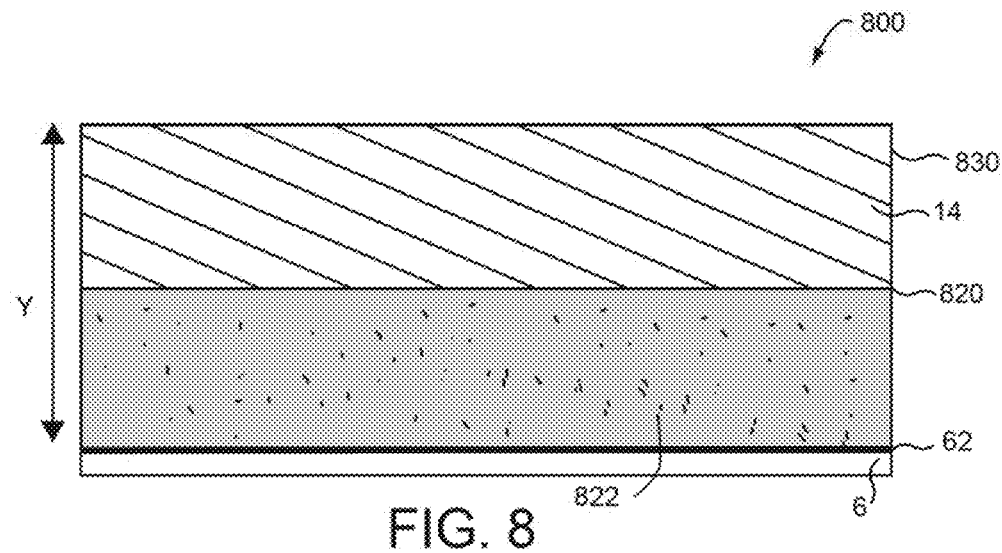
FIG. 8 is a diagrammatic illustration of another medical grade foam dressing, constructed according to the present invention.

Referring now to the drawings and more particularly to FIG. 8, there is shown a honey-dosed foam dressing 800, which is constructed in accordance with the present invention. Use of foam dressing 800 offers several advantages. For example, air passing through the foam regulates moisture levels at the wound site to further promote healing. Also, micro-holes in the foam act as air filters to keep debris and particulates out of the wound while simultaneously letting fresh air into the wound. Foam dressing 800 is substantially waterproof and quickly dries-out after getting wet. Also, the foam is flexible and stays in place when the body is in motion. In addition, the foam material is resilient, such that the foam material moves with the skin. This resiliency prevents the foam material from tearing and separating from the wound site due to skin movement. Also, thicker foam dressings provide cushioning that make inadvertent contact or impact with the wound site less painful.

As described in more detail herein below, honey dosed foam dressing 800 comprises a substrate 820 made of an absorbent foam material. The foam material 820 has a predetermined weight and thickness. Honey 14 is layered on one side of the foam substrate 820. Honey 14 has a predetermined weight as a percentage of the total weight of dressing 800. As with dressings 50 and 150, honey dosed foam dressing 800 is used as a wound dressing, wherein the honey layer contacts the wound site to promote healing of the wound when the dressing is applied.

The specific embodiment of the honey dosed foam dressing 800 will now be described. In this regard, and with reference to FIG. 8, honey dosed foam dressing 800 is a wound dressing comprising one or two components combined into a single unit. One component is a foam substrate 820. A second component is a fiber reinforcement 822 to provide stability to the foam substrate. The uncompressed density of foam substrate 820 is between 95-150 kg/m. Foam substrate 820 is, preferably, about 3-4 mm thick. Foam 820, preferably, is constructed of medical grade plastic polymer foam, such as polyether polyurethane foam.

Foam substrate 820 should have a thickness in a range (Y) of between 0.1 mm minimum to about a maximum of 25 mm, with a preferable thickness of approximately 4 mm.

With respect to FIG. 8, barrier 6, preferably is any suitable, breathable barrier constructed of polyurethane which is conventionally pre-coated with a medical grade medium tack acrylic or silicone pressure sensitive adhesive 62. While barrier 6 is cosmetic, the purposes of barrier 6 are to provide a barrier to stop bacterial infection from outside of the wound, to stop any honey 14 from potentially bleeding through barrier 6, to protect the dressing 800 from debris or liquid contamination and to stop exudates from bleeding through dressing 800. Preferably, the thickness of barrier 6 is around 30 microns. It is to be understood that barrier 6 can also be attached to gap-patterned dressing 800 by conventional heat bonding.

Another component is honey 14 disposed on one side of foam substrate 820, so that a honey layer 830 is created by an even disposition of honey 14 throughout foam substrate 820. Honey layer 830 is preferably less than about 75% by weight of the total weight of wound dressing 800. As with wound dressings 50 and 150, foam wound dressing 800 is applied such that honey layer 830 contacts the wound site to promote healing of the wound.

Figure 9:
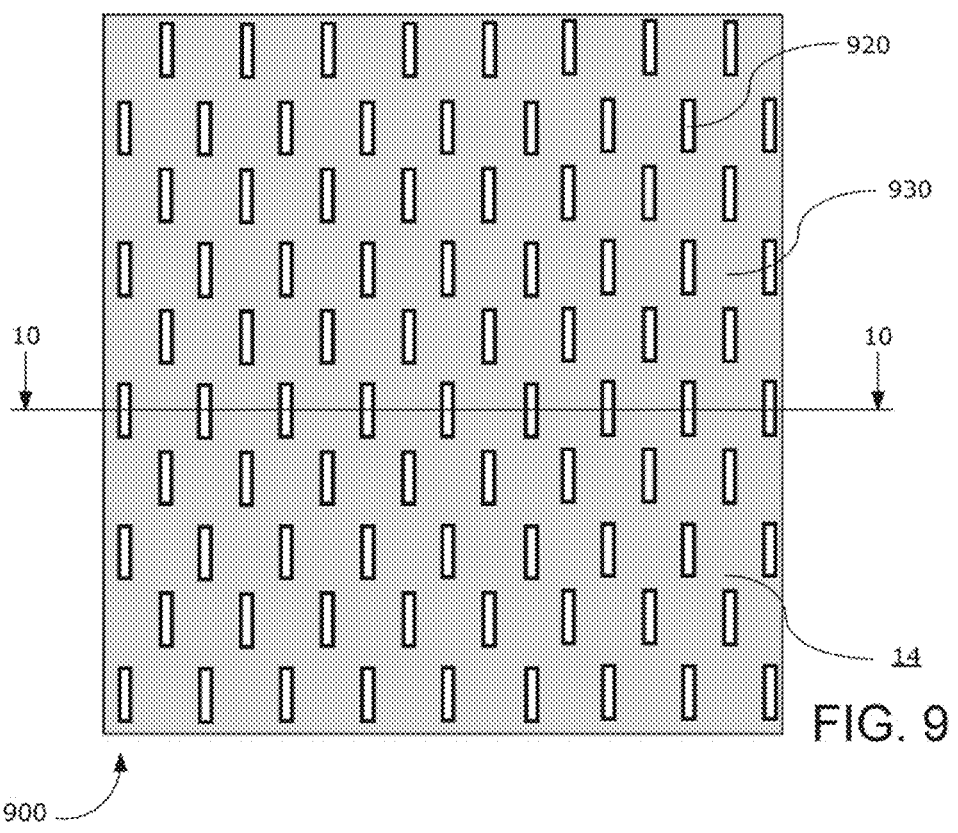
FIG. 9 is a top view of a medical grade gauze dressing with gaps in the structure of the gauze and an anti-tackiness protective layer on both sides, which is constructed in accordance with the present invention.
Figure 10:
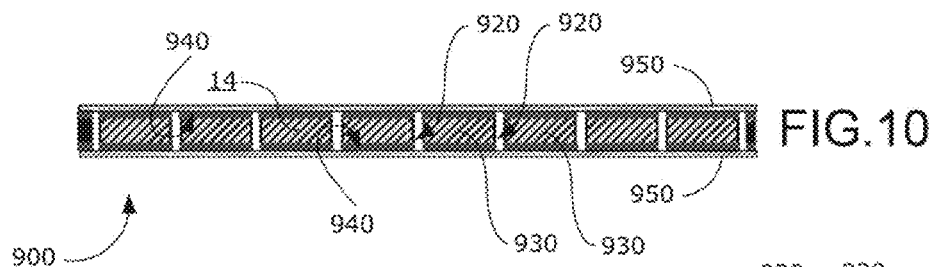
FIG. 10 is a cross-sectional view of the medical grade gauze dressing taken substantially along line 10-10 of FIG. 9.

Referring now to the drawings and more particularly to FIGS. 9-10, there is shown a honey-dosed gauze dressing 900, which is constructed in accordance with the present invention. As described in more detail herein below, honey dosed gauze dressing 900 comprises a material, such as gauze, which contains gaps in the gauze. The surface of the gauze is dosed with honey, such that the honey resides within the gauze between the gaps but substantially not in the gaps. As with dressings 50, 150 and 800, the side of the material containing the honey is placed on the wound to promote healing of the wound. An anti-tackiness coating, sheet or protective layer may or may not cover the honey.

Honey comb gauze dressing 900 exhibits several advantages. As stated herein above, the gauze contains the honey within its structure. This particular structure of the gauze holds more honey than standard honey dosed gauze dressings. The gaps in the gauze allow for greater expansion, conformity and flexibility of the dressing. Furthermore, the gaps allow for the free passage of exudate, if present, within the wound, so that this may be more quickly collected and managed by any absorbent materials surrounding the wound treatment zone. Also, in one embodiment, honey dosed gauze dressing 900 includes an anti-tackiness coating, sheet or protective layer covering the honey for reducing the risk that the dressing will undesirably adhere to the wound site and will provide the gauze with an anti-tackiness feeling to touch. However, the structure of the honey dosed gauze dressing 900 can advantageously eliminate the need for an anti-tackiness layer covering the honey and therefore, in another embodiment, the anti-tackiness layer is omitted. Finally, as previously discussed herein, the high sugar levels found in the honey, result in an osmotic pressure that promotes autolytic debridement.

Referring back to FIG. 9, honey comb gauze dressing 900 will now be described. In this regard, and with reference to FIG. 9, honey comb gauze dressing 900 includes a pattern of gaps 920 and surrounding fabric 930. The gauze dressing 900, preferably, has a weight of approximately 300 grams per meter squared.

Gauze dressing 900 is woven, knitted or structured so as to define a plurality of laterally adjacent linear shaped gaps 920 therein, illustrated with white background, as best seen in FIG. 9. Gaps 920 form a regular pattern similar to the parallel walls between the cells on a honey comb. In this manner, honey dosed gauze dressing 900 forms a matrix that may be considered analogous to the structure of a bee's honey comb.

Honey 14 is disposed into gauze dressing 900 in the fabric 930 to completely fill the structure around the gaps 920. For clarity of understanding the gauze dressing 900, the honey 14 is shown in FIGS. 9-10 as unobstructed shaded areas. The honey dose 14 is used, among other things, to reduce the risk of wound infection and to promote healing, as with dressings 50, 150 and 800. The preferred weight of honey dose for this presentation is between 65-70% of the total dressing weight.

Located on either side of gauze dressing 900 is an anti-tackiness coating, sheet or layer 940 and an additional protective cover 950 over honey dosed fabric 930. Anti-tackiness coating, sheet or layer 940 will reduce the risk that dressing 900 will undesirably adhere to the wound site. In this regard, anti-tackiness layer 940 should have a low stickiness property (i.e., low ability to retain solvents upon drying). Such an anti-tackiness layer 940 may comprise silicone oil, embossed or un-embossed polymer liners or other suitable anti-tackiness compositions. As shown in FIG. 9, anti-tackiness layer 940 may be on either or both sides of gauze dressing 900 and contacts the wound when honey dosed dressing 900 is applied.

Figure 11:
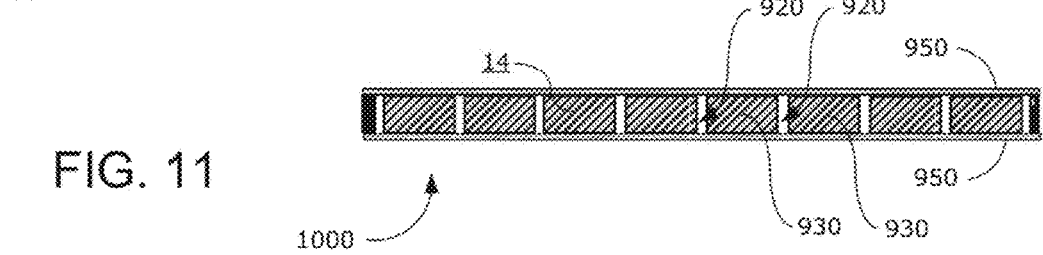
FIG. 11 is a diagrammatic illustration of the medical grade gauze dressing of FIG. 10 with the anti-tackiness layer removed.

Referring now to the drawings and more particularly to FIG. 11, a honey dosed gauze dressing 1000 is illustrated. The honey dosed gauze dressing 1000 is substantially similar to honey dosed gauze dressing 900 except, however, the structure of honey dosed gauze dressing 1000 allows for the elimination of anti-tackiness layer 940 (FIG. 9), if desired. The ability to eliminate the anti-tackiness layer 940 without affecting the functionality of honey dosed gauze dressing 1000 is due to the surface texture of the honey dosed gauze dressing 1000. It is also to be understood that the elimination of anti-tackiness layer 940 in honey dosed gauze dressing 1000 may also reduce the amount of material comprising the dressing and, therefore, may reduce manufacturing costs.

Figure 12:
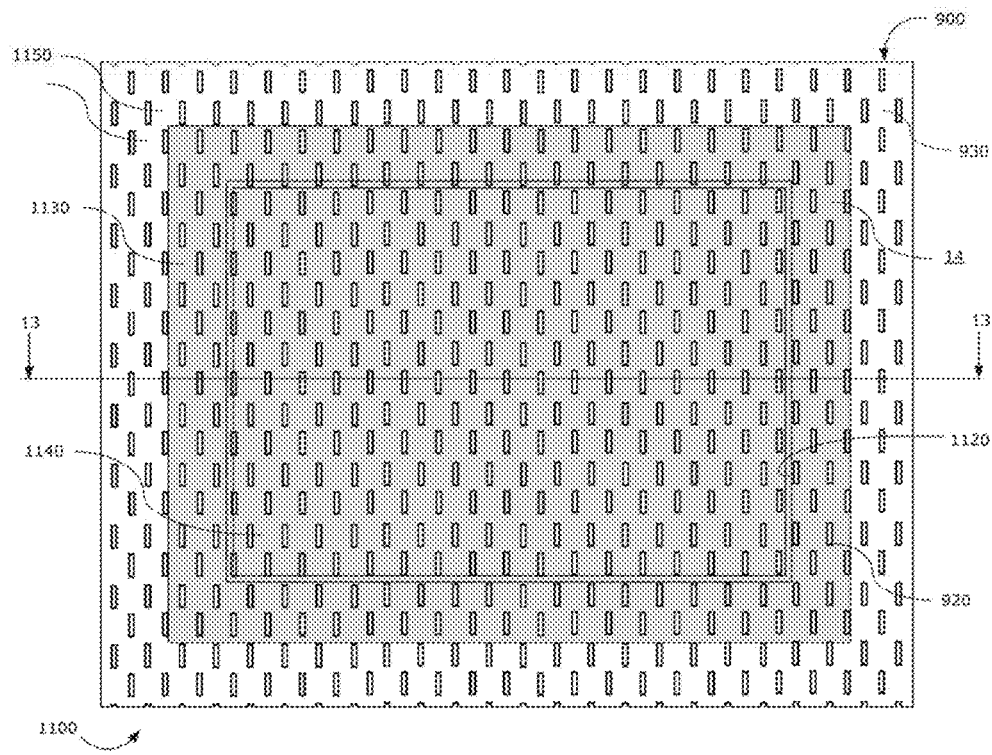
FIG. 12 is a diagrammatic illustration of a medical grade gauze dressing including a pouch in which an absorbent pad is located, which is constructed in accordance with the present invention.
Figure 13:
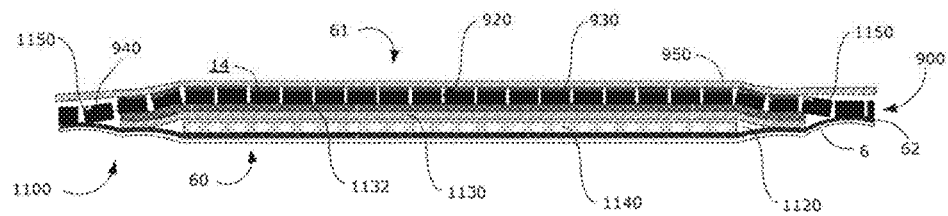
FIG. 13 is a cross-sectional view of the medical grade gauze dressing taken substantially along line 13-13 of FIG. 12.

Referring now to the drawings and more particularly to FIGS. 12-13, there is shown a honey dosed gauze dressing 1100, which is constructed in accordance with the present invention. As described in more detail herein below, honey dosed gauze dressing 1100, having a non-wound contact side indicated generally at 60 (FIG. 13) and a wound contact side indicated generally at 61 (FIG. 13), comprises a material, such as gauze, which contains gaps in the gauze, in combination with an absorbent pad located in a pouch attached to the gauze. The surface of the gauze is dosed with honey, such that the honey resides within the gauze around the gaps. As with dressings 50, 150, 800, 900 and 1000, the side of the material containing the honey is placed on the wound to promote healing of the wound. An anti-tackiness coating, sheet or protective layer may or may not cover the honey.

Honey dosed gauze dressing 1100 exhibits several advantages. As stated herein above, the gauze contains the honey within its structure. The gaps in the gauze allow for greater conformity and flexibility of the dressing. Furthermore, the gaps allow for the free passage of exudate from the wound, so that this can be collected and managed by the absorbent pad located within the pouch underneath the honey dosed gauze. The absorbent pad contains super absorbent powder to manage high levels of exudate, locking it within the secure pouch. The choice of the material for the wicking layer which forms one side of the pouch, between the honey dosed gauze and the absorbent pad, allows a slow initial transfer of exudate which thereby reduces the risk of painful wound treatment often associated with the application of super absorbent dressings. Maintaining a steady rate of transfer of exudate promotes the complete dispersal of honey throughout the wound treatment zone. Also, honey dosed gauze dressing 1100 includes a protective cover and a picture frame dry edge for ease of handling during application (FIG. 13). Finally, as previously discussed herein, the high sugar levels found in the honey, result in an osmotic pressure that promotes autolytic debridement.

Referring back to FIGS. 12-13, honey dosed gauze dressing 1100 will now be described. In this regard, and with reference to FIG. 13, honey dosed gauze dressing 1100 includes the same gauze described in dressing 900 above. A pouch 1120 is formed from an adhesive coated wicking layer 1130 and the polyurethane barrier 6, as described more fully for dressing 50, which forms the backing to dressing 1100. Inside the pouch 1120, an absorbent pad 1140 is located to collect and manage exudate from the wound. The wicking layer 1130 has an acrylate adhesive 1132 which has the necessary wet performance properties to regulate the flow of exudate through the dressing.

Gauze 900 is woven, knitted or structured so as to define a plurality of laterally adjacent linear shaped gaps 920 therein, illustrated with white background, as best seen in FIG. 9. Gaps 920 form a regular pattern similar to the parallel walls between the cells on a honey comb. In this manner, honey dosed gauze dressing 900 forms a matrix that may be considered analogous to the structure of a bee's honey comb.

Honey 14 is disposed into gauze 900 in the fabric 930 to completely fill the structure apart from the gaps and the picture frame dry edge feature shown more clearly in FIG. 12. For clarity of understanding the gauze dressing 1100, the honey 14 is shown in FIG. 12 as unobstructed shaded areas. The honey dose 14 is used, among other things, to reduce the risk of wound infection and to promote healing, as with dressings 50, 150, 800, 900 and 1000. The preferred weight of honey dose for this presentation is between 45-65% of the total dressing weight. Finally, it is to be understood that dressing 1100 may not include dry edges 1150.

Located on the wound contact face 61 of dressing 1100 is an anti-tackiness coating, sheet or layer 940 and an additional protective cover 950 over honey dosed fabric 930. Anti-tackiness coating, sheet or layer 940 will reduce the risk that dressing 1100 will undesirably adhere to the wound site. In this regard, anti-tackiness layer 940 should have a low stickiness property (i.e., low ability to retain solvents upon drying). Such an anti-tackiness layer 940 may comprise silicone oil, or other suitable anti-tackiness compositions. It is to be understood that, as described above for dressing 1000, the anti-tackiness layer 940 may not be included in dressing 1100 which will reduce manufacturing costs, without affecting the functionality of dressing 1100, due to the surface texture of the gauze 900.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved honey dosed, patterned foam dressing and a novel method of using the honey dosed, patterned foam dressing. The preferred honey dosed, patterned foam dressing according to various embodiments of the present invention, offers the following advantages; ease of use, improved dressing strength, reduced dressing weight, increased efficiency and controlled lay down of honey, increased ability to deliver an equal measure of honey across the wound bed; increased ability to promote controlled, naturally occurring osmotic delivery action of the honey onto the wound bed; increased rate of absorption of exudates while allowing honey stored within the honey-dosed area to flow naturally onto the wound, and improved ease of handling of the dressing. In fact, in many of the preferred embodiments, these factors of improved strength, reduced weight, increased lay down efficiency, increased honey loading, increased honey delivery, increased osmotic delivery action, increased exudate absorption ability, and improved ease of handling are optimized to an extent that is considerably higher than heretofore achieved in prior, known honey-based wound dressings.

We claim:

1. A wound dressing, comprising;
a sheet of absorbent foam having a patterned and a non-patterned side;
wherein the patterned side is provided with an applied pattern of a plurality of honey dosed foam areas;
wherein the applied pattern of said plurality of honey dosed foam areas for, a plurality of non-honey dosed absorbent areas in the patterned side of said sheet of absorbent foam; and
wherein when the wound dressing is applied to a wound treatment zone said non-honey dosed absorbent areas expand thereby applying a physical pressure to adjacent individual ones of said plurality of honey dosed foam areas thereby causing honey disposed therein to be discharged into the wound treatment zone.

2. The wound dressing, as in claim 1 wherein the sheet of absorbent foam includes a dry edge portion disposed substantially along any outer side edge of the sheet of absorbent foam which allows for ease of handling without, contacting honey or exudate disposed in the wound dressing.

3. The wound dressing, as in claim 1, wherein the individual ones of the honey dosed foam areas are hexagon-shaped areas.

4. The wound dressing, as in claim 1, wherein the sheet of absorbent foam is comprised of a medical grade, porous polymeric foam.

5. The wound dressing, as in claim 4, wherein the polymeric foam is further comprised of: a medical grade polyether polyurethane foam.

6. The wound dressing, as in claim 1, wherein the sheet of absorbent foam includes a thickness that is sufficient to hold a specific amount of honey about 50% by total weight to about 75% by total weight of the sheet of absorbent foam and honey, in combination.

7. The wound dressing, as in claim 6, wherein the thickness of the sheet of absorbent foam is between 0.1 mm and 25 mm.

8. The wound dressing, as in claim 1, wherein the honey dosed foam areas are dosed with honey selected from a group of different honeys consisting of: medical grade Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, Acacia, Spanish Blossom, Tasmanian Leatherwood, Organic Honey All, New Zealand Beach, Kanuka, New Zealand Bush New Zealand Honeydew, Jarrah, Thyme, and Kemahi honeys.

9. The wound dressing, as in claim 1, wherein a width dimension of each individual one of said plurality of the honey dosed foam areas is between 0.05 mm and 100 mm.

10. The wound dressing, as in claim 1, wherein said patterned side of the sheet of absorbent foam is layered with a minimal trace of honey.

11. The wound dressing as in claim 10, wherein the dressing further comprises:
a peelable protective liner overlaid on said patterned side of the sheet of absorbent foam.

12. The wound dressing, as in claim 11, wherein said peelable protective liner is secured to the patterned side of the sheet of absorbent foam by the minimal trace of honey.

13. The wound dressing, as in claim 1, wherein the non-patterned side of the sheet of absorbent foam includes a breathable barrier.

14. The wound dressing, as in, claim 13, wherein the breathable barrier, is secured to the non-patterned side of the sheet of absorbent foam by an adhesive.

15. The wound dressing, as in claim 1, wherein the dressing is enclosed a protective pouch to provide a moisture barrier for protecting the dressing.

16. A method for preparing and using a patterned foam dressing, comprising the steps of:
providing a sheet of absorbent foam;
applying to one side of said sheet of absorbent foam a pattern of a plurality of honey dosed foam areas;
wherein the applied pattern of said plurality of honey dosed foam areas form a plurality of absorbent, non-honey dosed areas on the one side of said sheet of absorbent foam; and
applying the one side of said sheet of absorbent foam to a wound treatment zone to allow the non-honey dosed absorbent areas to expand by absorbing wound exudates from the wound treatment zone which thereby causes a physical pressure to be applied to adjacent individual ones of said plurality of honey dosed foam areas which thereby causes honey disposed therein to be discharged into the wound treatment zone.

17. The method, as in claim 16, wherein the applying a pattern of a plurality of honey dosed foam areas step is further comprised of the step of: applying specific amounts of honey to a flat, flexible and planar sheet of absorbent foam such that the plurality of absorbent, non-honey dosed foam areas, and honey-dosed areas are consequently formed along the patterned side of the absorbent foam by the application of the honey to the sheet of absorbent foam.

18. The method, as in claim 17, wherein the applying specific amounts of honey step is further comprised of: applying the honey by coating, dosing, pasting, impregnating, injecting, pouring, spraying, transferring, printing (all methods) including lithography, stenciling, flexography, gravure, infusion, and rotogravure.

19. The method, as in claim 16, wherein the method is further comprised of the step of: attaching a barrier to a non-patterned side of the absorbent foam.

20. The method, as in claim 16, wherein the method is further comprised of the step of: locating a protective liner adjacent to the patterned side of the absorbent foam.

21. A gap-patterned wound dressing, comprising:
a patterned, absorbent foam structure having a gap-patterned side and a non-gap patterned side, wherein the gap-patterned side includes a pattern of absorbent foam, non-honey dosed gaps disposed between absorbent foam areas dose with honey;
wherein, when the gap-patterned wound dressing is applied to a wound treatment zone, said absorbent foam, non-honey dosed gaps expand thereby applying a physical pressure to adjacent individual ones, of said plurality of absorbent foam areas dosed with honey thereby causing honey disposed therein to be discharged into the wound treatment zone; and wherein the patterned, absorbent foam structure includes a thickness that is sufficient to hold a specific amount of honey about 50% by total weight to about 75% by total weight of the patterned, absorbent foam structure and honey, in combination.

22. A wound dressing, comprising:

an absorbent foam, having a wound contact side and a non-wound contact side, wherein said wound contact side is provided with an applied pattern of a plurality of honey dosed foam areas to form a plurality of absorbent, non-honey dosed areas;

wherein, when the applied pattern of said plurality of honey dosed foam areas and said plurality of absorbent non-honey dosed areas of the wound dressing are applied to a wound treatment zone, said absorbent, non-honey dosed areas expand thereby applying a physical pressure to adjacent individual ones of said plurality of honey dosed foam areas thereby causing honey disposed therein to be discharged into the wound treatment zone;

wherein the wound contact side is dosed with an amount of honey that ranges from about 50% by total weight of honey to about 75% by total weight of honey to the total weight of the absorbent foam and honey, in combination; and wherein the non-wound contact side is provided with a breathable polyurethane barrier.

23. A honey dosed foam wound dressing comprising:

a composite fiber reinforced, absorbent, foam structure and a non-patterned side;

wherein the patterned side is provided with an applied pattern of a plurality of honey dosed foam areas;

wherein the applied pattern of said plurality of honey dosed foam areas form a plurality of non-honey dosed, absorbent areas in the patterned side of said absorbent foam;

wherein, when the wound dressing is applied to a wound treatment zone, said non-honey dosed, absorbent areas expand thereby applying a physical pressure to adjacent individual ones of said plurality of honey dosed foam areas thereby causing honey disposed therein to be discharged into the wound treatment zone; and wherein the honey dosed foam areas are dosed with, an amount of honey that is less than about 50% by weight of the total weight of wound dressing.

24. The honey dosed wound dressing, as in claim 23, wherein the composite fiber reinforced. absorbent, foam structure has an uncompressed density of approximately between 95-150 kg per meter cubed.

* * * * *

UNITED STATES PATENT AND TRADEMARK OFFICE
CERTIFICATE OF CORRECTION

PATENT NO. : 9,358,256 B2
APPLICATION NO. : 13/939829
DATED : June 7, 2016
INVENTOR(S) : Greg Devenish et al.

It is certified that error appears in the above-identified patent and that said Letters Patent is hereby corrected as shown below:

In the claims,

Claim 1, column 17, line 27, change "for," to ""form".

Claim 2, column 17, line 39, cancel the "," after the text beginning with "which allows for ease of handling without".

Claim 14, column 18, line 17, cancel the "," after the text beginning with "as in".

Claim 14, column 18, line 18, cancel the "," after the text beginning with "breathable barrier".

Claim 21, column 18, line 65, change "dose" to "dosed".

Signed and Sealed this
Ninth Day of August, 2016

Michelle K. Lee
*Director of the United States Patent and Trademark Office*